United States Patent [19]
Sharma et al.

[11] Patent Number: 5,800,897
[45] Date of Patent: Sep. 1, 1998

[54] AIR FRESHENER COMPOSITION CONTAINING A FIBER PAD

[75] Inventors: Mahendra Kumar Sharma; Richard Irving Garrity; John Jacob Hiller, all of Kingsport, Tenn.

[73] Assignee: Eastman Chemical Company, Kingsport, Tenn.

[21] Appl. No.: 599,488

[22] Filed: Jan. 25, 1996

[51] Int. Cl.$^6$ .......................................... B32B 1/04
[52] U.S. Cl. ........................ 428/74; 428/74; 428/76; 428/120; 428/397; 428/400; 239/53; 239/54; 239/55
[58] Field of Search .................... 428/74, 76, 120, 428/397, 400; 239/53, 54, 55

[56] References Cited

U.S. PATENT DOCUMENTS

| | | | |
|---|---|---|---|
| 4,708,900 | 11/1987 | Siegers et al. | 428/74 |
| 5,261,870 | 11/1993 | Hammerstedt et al. | 600/35 |
| 5,268,229 | 12/1993 | Phillips et al. | 428/400 |
| 5,297,732 | 3/1994 | Hahn | 239/55 |

FOREIGN PATENT DOCUMENTS

WO 92 05713 A  4/1992  WIPO.

OTHER PUBLICATIONS

Database WPI, Section Ch, Week 9433, Derwent Publications Ltd., London, GB; Class A94, AN 94–269834, XP002032134 & JP 06 200 459 A (Toyobo KK), 19 Jul. 1994, see Abstract.

Database WPI, Section Ch, Week 9329, Derwent Publications Ltd., London, GB; Class A96, AN 93–231545, XP002032135 & JP 05 154 174 A (Kanebo Ltd), 22 Jun. 1992, see Abstract.

Database WPI, Section Ch, Week 8712, Derwent Publications Ltd, London, GB; Class A60, AN 87–083156, XP0020322136 & JP 62 033 854 A (Daiwa Spinning Co Ltd), 13 Feb. 1987, see Abstract.

*Primary Examiner*—Richard Weisberger
*Attorney, Agent, or Firm*—Andrew B. Griffis; Harry J. Gwinnell

[57] ABSTRACT

This invention is directed to an air freshener composition containing a fiber pad comprising at least one needle-punched, nonwoven, hydrophilic fiber wherein the fiber has a capillary structure and deep grooves or channels along the longitudinal axis of the fiber, a fragrance incorporated into said fiber pad, wherein the fiber pad is enclosed by a container having air passageways to allow for the fragrance to escape into the surrounding environment.

16 Claims, No Drawings

5,800,897

AIR FRESHENER COMPOSITION CONTAINING A FIBER PAD

FIELD OF THE INVENTION

This invention is directed to an air freshener composition containing a fiber pad comprising at least one needle-punched, nonwoven, hydrophilic fiber wherein the fiber has a capillary structure and deep grooves or channels along the longitudinal axis of the fiber, a fragrance incorporated into said fiber pad, wherein the fiber pad is enclosed by a container having air passageways to allow for the fragrance to escape into the surrounding environment.

BACKGROUND OF THE INVENTION

Air fresheners are available for room and automobile applications. Generally air fresheners can be used at room temperature, but in high temperature applications, for example in automobiles, the fragrance does not last more than two weeks since the fragrance release rate increases with temperature. Accordingly, it is desirable to develop an air freshener which provides mild fragrance in high temperature applications and retains the fragrance smell for a period of 8 to 10 weeks.

U.S. Pat. No. 5,297,732 discloses a fragrance emitting container having a container body which encloses a container space, a channel in the container body, a fragrance reservoir containing a fragrance positioned in the channel, and a container lid pivotally attached to the container body. The container lid may either cover the container space and partially seal the fragrance reservoir well, or may be in an open position wherein the subcontainer space and subcontainer fragrance reservoir are uncovered. The fragrance emitter is incorporated into the container so that the container contents can be kept free of fragrance producing chemicals.

U.S. Pat. No. 5,261,870 discloses a separation barrier having pores or micropores which are initially plugged with one or more materials selected for their solubility relative to certain environmental conditions. The pores or micropores are initially filled with a material having greater erodibility than the material constituting the separation barrier itself. The barrier material may be used as an indoor air freshener.

U.S. Pat. No. 5,268,229 discloses filaments having "U" and "E" shaped cross-sections with stabilizing legs which spontaneously transport aqueous fluids on the surface thereof. The filaments are useful in absorbent articles. U.S. Pat. No. 5,268,229 does not disclose the use of such filaments in air freshener compositions.

SUMMARY OF THE INVENTION

The present invention relates to an air freshener composition useful for ambient and high temperature applications. The air freshener composition comprises:

(A) 1 to 75 weight percent of a fiber pad comprising at least one needle-punched, nonwoven, hydrophilic fiber wherein the fiber has a capillary structure and deep grooves or channels along the longitudinal axis of the fiber; and (B) 25 to 99 weight percent of at least one fragrance incorporated into said fiber pad, wherein the fiber pad is enclosed by a container having air passageways to allow for the fragrance to escape into the surrounding environment.

DESCRIPTION OF THE INVENTION

The present invention is directed to an air freshener composition useful for ambient and high temperature applications such as automobile applications wherein temperatures may reach up to about 280° F. The air freshener composition contains a mixture of selected fragrances for desired smell impregnated in a pad. The fragrances are loaded in the pad either at room temperature or at elevated temperature depending on the state of the mixture of selected fragrances.

The fiber pads are prepared from needle-punched, nonwoven fibers. The fibers are selected from polymers such as polyesters including copolyesters, cellulose acetate, olefins, nylon, modacrylate, polyphenylene sulfide, viscose rayon, fibers made from biodegradable materials, and suitable mixtures or blends thereof. Preferred fibers are polyesters and copolyesters which are selected from relatively oriented polyesters, relatively un-oriented polyesters, polyesters containing starch, polyesters containing cellulose acetate, polyesters containing cellulose propionate, polyesters containing cellulose butyrate, polyesters containing modified starch (e.g. starch acetate), polyesters containing biodegradable materials, and aliphatic polyesters blended with cellulose esters. Moreover, polyesters which have been modified chemically or by a polymerized exterior coating can be used as a fiber pad for loading fragrances to prepare the air freshener compositions.

Cellulose acetate fibers can be prepared by melt-spinning or conventional solvent-spinning means using acetone as a solvent. The cellulose acetate may contain additives which further enhance hydrophilic action and/or other desired properties.

Polyesters and copolyesters are prepared by polymerizing dicarboxylic acids or esters thereof and glycols. Suitable dicarboxylic acids include: terephthalic acid, isophthalic acid, p,p'-diphenyldicarboxylic acid, p,p'-dicarboxydiphenyl ether, p,p'dicarboxydiphenyl hexane, p,p'-dicarboxydiphenyl ether, and p,p'-dicarboxyphenoxy ethane, and the dialkylesters thereof that contain 1 to 5 carbon atoms in the alkyl groups.

Suitable aliphatic glycols are acyclic and alicyclic aliphatic glycols having 2 to 10 carbon atoms, preferably those represented by the general formula $HO(CH_2)_nOH$, wherein n is an integer having a value of 2 to 10. For example, ethylene glycol, trimethylene glycol, tetramethylene glycol, pentamethylene glycol, and decamethylene glycol. Aliphatic glycols also include: 1,4-cyclohexanedimethanol, 3-ethyl 1,5-pentanediol, 1,4-xylene, glycol, and 2,2,4-4 tetraethyl 1,3-cyclobutanediol. A hydroxylcarboxyl compound such as 4-hydroxybenzoic acid, and 4-hydroxyethoxybenzoic acid, may also be used.

Mixtures of the dicarboxylic acids and/or mixtures of the aliphatic glycols can be used. A minor amount of the dicarboxylic acid component, generally up to about 10 mole percent, can be replaced by other acids or modifiers such as adipic acid, sebacic acid, or the esters thereof, or with modifiers that impart improved dyeability or dyeability with basic dyes to the polymers.

The most preferred polymers for use in the present invention are (1) relatively unoriented and relatively oriented polyethylene terephthalate (PET); (2) co-polyesters based on polyethylene terephthalate, particularly those suitable for use as binder fibers, (3) polyethylene terephthalate containing cellulosic additives and/or modified starch, such as starch acetate, and (4) cellulose acetate.

The fibers are preferably non-round fibers having at least one continuous groove such as those disclosed in U.S. Pat. No. 5,268,229, the disclosure of which is incorporated in its entirety herein by reference. The surface of the groove or channel is most preferably rougher than the surface outside the groove. The grooves can be arranged in a circular pattern around a solid or hollow core. The preferred non-round fiber has at least 1 to 30 grooves and/or channels and/or legs which are substantially continuous. Fibers having a plurality of grooves have a larger surface area per unit weight than round fibers and thus can be coated with more lubricant. Fibers having at least one continuous cross-sectional groove preferably have at least 0.3 wt. % lubricant coated on their surfaces whereas fibers having five or more grooves have at least 0.5 wt. % lubricant coated on their surfaces.

A preferred fiber useful in the air freshener composition is a tow of continuous filaments of between about 10,000 up to at least 100,000 total denier. However, tows of much greater denier can also be used. The tow (crimped or non-crimped) can be processed through a tow feeder after the tow dryer (skipping the cutter) and collected in a baler to form bales which are convenient for shipment. The tow subsequently can be opened or spread by rolls and/or jets and thereafter used in various nonwoven products, filters, etc. For staple fibers, the total tow denier can be as small as 30,000 and as large as at least 2,000,000. It is also preferred that the fiber of the present invention be subjected to crimping immediately after being contacted and spread with the heated solution of processing lubricant. The preferred crimped fiber has a staple length of about 0.5 cm to about 15 cm and/or a denier per filament of about 0.7 to 200.

The treated fibers in the form of tow, crimped staple or uncrimped staple can be subsequently blended or combined with at least one other tow or staple fiber (such as a binder fiber); subjected to suitable nonwoven processing to form a web with the web being subsequently heated and appropriately compressed to cause the blended fibers to compress and bond so as to produce a bonded, nonwoven material, such as a fabric or batting.

The surface of the fiber may be modified by the addition of a lubricant. A process of applying the lubricant on the surface of the fiber entails contacting a group of fibers arranged in a relatively flat band (drawn or entrain tow) with at least one of certain processing lubricants at an elevated temperature; causing the processing lubricant to penetrate into the tow to cost the fibers; subsequently subjecting the tow to pressure via driven rolls followed by heating the tow at a temperature for a time sufficient to bake or dry said lubricant onto and/or into the surface of the fibers. The driven rolls can be the rolls of a crimper.

It is preferred that the fiber useful in the air freshener composition has a hydrophilic lubricant coated on the surface thereof. Particularly preferred hydrophilic lubricants which can be used to lubricate the fibers include the following:

(1) Lubricant comprising 49% polyethylene glycol (PEG) 600 monolaurate, polyoxyethylene (13.64) monolaurate, 49% polyethylene glycol (PEG) 400 monolaurate, polyoxyethylene (9.09) monolaurate, and 2% of 35% active 4-cetyl-4-ethylmorpholinium ethosulfate (antistat);

(2) Hypermer A109 sold by ICI Americas, Inc., which is a modified polyester surfactant;

(3) Milease T sold by ICI Americas, Inc. which is a soil release agent comprising polyester, water, and other ingredients;

(4) Brij 35 sold by ICI Americas, Inc. which is a polyoxyethylene (23) lauryl ether;

(5) Brij 99 sold by ICI Americas, Inc. which is a polyoxyethylene (20) oleyl ether;

(6) G-1300 sold by ICI Americas, Inc. which is a polyoxyethylene glyceride ester, a nonionic surfactant;

(7) G-1350 sold by ICI Americas, Inc., a polyoxylene-polyoxypropylene sorbitan linoleic phthalic ester; and (8) Lubricant comprising 49% polyethylene glycol (PEG) 600 monolaurate, polyoxyethylene (13.64) monolaurate, 49% polyethylene glycol (PEG) 400 monolaurate, polyoxyethylene (9.09) monolaurate, 2% of 35% active 4-cetyl-4-ethylmorpholinium ethosulfate (antistat), and optionally a refrigerant.

More preferably the polyester is poly(ethylene terephthalate) and the hydrophilic lubricant is a potassium lauryl phosphate based lubricant comprising monolaurate which is uniformly applied at a level of at least about 0.05%, preferably at least 0.5%, by weight of the total fiber.

A preferred process for helically crimping the fibers which make up the fiber pad involves the following steps: extruding a conventional PET fiber forming polymer; passing the polymer through spinneret hole shapes; orienting said spinneret hole shapes to the cross-flow quench air so that quenching occurs perpendicular to the major axis of the fiber; controlling the quench air; applying hydrophilic lubricants; taking up the fibers at conventional speeds; drafting the fibers using conventional drafting (single steam stage in steam or two stage in water and steam); adding an additional amount of hydrophilic lubricant; and relaxing the drawn fibers in a heated chamber to develop the helical crimp. It is preferred that the number of crimps/inch in the fiber is greater than 4 and the crimp amplitude is less than 2 mm.

The fibers are prepared from filaments which are capable of spontaneously transporting fluids. The filaments are described by the following equation $$(1-X \cos \theta_a) < 0$$

wherein $\theta_a$ is the advancing contact angle of water measured on a flat film made from the same material as the filament and having the same surface treatment, if any. The letter X is a shape factor of the filament cross-section that satisfies the following equation $$X = \frac{P_w}{4r + (\pi - 2)D}$$

In the above equation, $P_w$ is the wetted perimeter of the filament. The letter r is the radius of the circumscribed circle circumscribing the filament cross-section. The letter D is the minor axis dimension across the filament cross-section.

The term "spontaneously transportable" and derivative terms thereof refer to the behavior of a fluid in general and in particular a drop of fluid, typically water, when it is brought into contact with a single filament such that the drop spreads along the filament. Such behavior is contrasted with the normal behavior of the drop which forms a static ellipsoidal shape with a unique contact angle at the intersection of the liquid and the solid filament. The key factor is the movement of the location of the air, liquid, solid interface with time. If the interface moves just after contact of the liquid with the filament, then the filament is spontaneously transportable; if the interface is stationary, the filament is not spontaneously transportable. The spontaneously transportable phenomenon is visible to the naked eye for filaments having a denier per filament (dpf) of greater than 20. The filaments of the present invention preferably have a dpf of about 3 to about 1,000, more preferably 5 to 30.

Preferably, the polyester fibers can be characterized by the following properties:

| Fiber Denier | 6 | 10 | 15 |
|---|---|---|---|
| Fiber Shape Factor* | 2.7 | 2.7 | 2.4 |
| Specific Surface Area, cm2/g** | 3130 | 2210 | 1710 |
| Main Groove Width, microns | 8 | 10 | 12 |
| Main Groove Depth, microns | 13 | 18 | 21 |
| Specific Capillary Volume, cm3/g*** | 0.49 | 0.47 | 0.39 |
| Groove Area, percent**** | 40 | 40 | 35 |

*Ratio of perimeter of fiber to that of round fiber, same d/f
**Ratio of fiber perimeter to fiber cross-sectional area × 1/polymer density
***Ratio of groove to fiber cross-sectional area × 1/polymer density. Equates to grams of water the filled grooves can theoretically hold per gram of fiber.
****Ratio of groove to (groove + fiber) cross-sectional area × 100

The fiber pads can be made by laying-down a series of fibers. The fibers can be blown onto, for example, an absorbent core made from cellulosic fibers, or multiple capillary channel fibers may be formed into a batt or pad, said pad comprising a network of multiple capillary channel fibers. Such multifiber pads will typically have a caliper in the range from about 0.1 in. (0.254 cm) to about 0.7 in. (1.78 cm), preferably from about 0.1 in. (0.254 cm) to about 0.5 in. (1.27 cm) for use in air fresheners.

The fiber pads are loaded with fragrances to form an air freshener. Natural and/or synthetic fragrances including combinations thereof can be used to generate the desired smell. The fragrances can be divided based on their organoleptic properties as follows: alliaceous, animal, balsamic, camphoraceous, chemical, cherry, citrus, coffee, earthy, ethereal, fatty, floral, fruity, green, herbaceous, lemon, meaty, medicinal, minty, mossy, musty, new car scent, nutty, pepper, pine, pineapple, potpourri, smoky, soapy, spicy, sulfurous, vegetable, vanilla, waxy, wine-like, and woody.

The alliaceous category includes onion and garlic smell. The compounds used for these fragrances include: allyl disulfide, allyl mercaptan, allyl sulfide, butyl sulfide, 3-(methylthio)propionaldehyde, furfuryl isopropyl sulfide, methyl propyl disulfide, propyl disulfide, o-toluenethiol, cyclopentanethiol, dimethyl trisulfide, ethyl thioacetate, methyl thiobutyrate, methyl 2-thiofuroate, allyl thiopropionate, furfuryl thiopropionate, methyl furfuryl disulfide, dicyclohexyl disulfide, 1-butanethiol, propyl mercaptan, 4-(methylthio)butanol, benzenethiol.

The animal category of the fragrance includes the following compounds: indole, piperidine, piperine, skatole, valeric acid, vanillylacetone, isovaleric acid, methyl thiobutyrate, pyrrolidine, ethyl 3-(furfurylthio) propionate, ethyl 3-mercaptopropionate.

The balsamic category of the fragrances is subdivided as anise, balsam, caramel, chocolate, cinnamon, honey and sweet. The anise fragrances use ethyl acetate, methyl p-anisate, methy l3-phenylpropionate, p-tolyl acetate, γ-valerolactone, 3,4-dimethyl-1,2-cyclopentadione, 2-methoxy-4-propylphenol, vanillyl alcohol compounds. The balsam fragrance can be achieved by using allyl cinnamate, benzoic acid, cinnamyl alcohol, cinnamyl butyrate, cinnamyl isobutyrate, cinnamyl formate, cinnamyl propionate, cinnamyl isovalerate, ethyl 2-acetyl-3-phenylpropionate, β-ionone, phenethyl salicylate, 3-phenyl-1-propanol, 3-phenylpropylisobulyrate, piperonal, vanilln acetate, trans-2-methyl-2-butenoic acid, phytol, phenyl salicyclate, cis-3-hexenyl salicylate compounds. The caramel fragrance can be formulated using acetanisole, anisyl alcohol, 2-ethylbutyric acid, ethyl(±)-3-phenylglycidate, γ-heptalactone, 1-(p-methoxyphenyl)2-propanone, phenethyl acetate, pyruvaldehyde, tetrahydrofurfuryl propionate, 2-thiophenethiol, vanillin, 5-ethyl-3-hydroxy-4-methyl-2 (5h)-furanone, 4-hydroxybutanoic acid lactone, ethyl maltol, 2-oxobutyric acid, 5-(hydroxymethyl)fufural compounds. The chocolate fragrance can be formulated using anisyl alcohol, benzyl cinnamate, isobutyl hexanoate, benzyl ether, maltol, 2-methylbutyraldehyde, vanillin, 2-ethyl-3,5 (or 6)-dimethylpyrazine, 3-ethyl-2-hydroxy-2-cyclopenten-1-one, 5-methyl-2-phenyl-2-hexenal, 4-methyl-2-phenyl-2-pentenal, 2,3,5,6-tetramethylpyrazine, 2,3,5-trimethylpyrazine, 2-methoxypyrazine, 4-methyl-5-vinylthiazole, 2,4,5-trimethylthiazole, butyl-12-methylbutyrate, 3-methyl-1-pentanol compounds. The cinnamon fragrance can be formulated by using cinnamaldehyde, cinnamic acid, ethyl cinnamate, isoeugenyl phenylacetate, α-methylcinnamaldehyde, hydrocinnamaldehyde, 2,4-heptadienal compounds. The honey fragrance can be formulated by using allyl phenoxyacetate, allyl phenylacetate, butyl phenylacetate, citronellyl valerate, isoeugenyl phenylacetate, lauryl alcohol, methyl myristate, methyl3-phenylpropionate, 2-methylundecanal, octyl isovalerate, phethyl acetate, phenethyl alcohol, phenethylanthranilate, phenethyl benzoate, 2-phenoxyethyl isobutyrate, phenylacetic acid, propyl phenylacetate, isopropyl phenylacetate, myrtenal, isoamyl isobutyrate compounds. The sweet fragrance can be formulated by using acetanisole, acetophenone, allyl cyclohexanepropionate, allyl nonanoate, allyl phenylacetate, amyl alcohol, isoamyl hexanoate, amyl octanoate, anisyl formate, benzyl benzoate, benzyl propionate, isobutyl acetate, butyl anthranilate, isobutyl cinnamate, isobutyl formate, butyl lactate, (−)carvyl propionate, cinnamic acid, cinnamyl alcohol, cinnamyl isobutyrate, citronellyl butyrate, cyclohexaneethyl acetate, cyclohexyl propionate, benzyl ether, 2',4'-dimethylacetophenone, 3,7-dimethyl-1-octanol, 4-allylanisole, p-ethoxybenzaldehyde, ethyl acetoacetate, ethyl anthranilate, ethyl cinnamate, ethyl cyclohexanepropionate, ethyl3-methyl-3-phenylglycidate, ethyl phenylacetate, ethyl salicylate, ethyl vanillin, isoeugenol, isoeugenyl phenylacetate, furfural, geraniol, geranyl acetate, γ-heptalactone, 3-heptanone, heptyl butyrate, γ-hexalactone, 2,3-hexanedione, trans-2-hexenal, hexyl acetate, hexyl butyrate, 4-(p-hydroxypenyl)-2-butanone, lauric aldehyde, menthyl isovalerate, p-anisaldehyde, 2-methoxy-4-methylphenol, 4-(p-methoxyphenyl)2-butanone, 4-(3, 4-methylenedioxyphenyl)-2-butanone, methyl4-methylvalerate, 4-methyl-1-phenyl-2-pentanone, methyl salicylae, myrcene, neryl acetate, neryl butyrate, neryl isobutyrate, neryl isovalerate, phenethyl butyrate, benzylideneacetone, 3-phenylpripionic acid, 2-phenylpropyl butyrate, piperidine, propenyl guaethol, 1-propanol, isopropyl acetate, propyl formate, 3-propylidenephthalide, 1-phenyl-2-pentanol, isoquinoline, terpinyl formate, tributyl acetylcitrate, triethyl citrate, 10-undecenal, undecyl alcohol, vanillylacetone, 2-ethyl-1-hexanol, trans-2-hexenoic acid, o-methoxycinnamaldehyde, isopropyl tiglate, undecylenic acid, myrtenal, 4-oxoisophorone, 3-acetylpyridine, 2,4-dimethylbenzaldehyde, ethyl maltol, isophorone, 2-methoxy-4-propylphenol, 4,5-dimethyl-3-hydroxy-2,5-dihydrofuran-2-one, 2-ethylfuran, 6-amyl-α-pyrone, isoeugenyl benzyl ether, vanillyl alcohol, 4-ethylbenzaldehyde, myrtenyl acetate, p-anisic acid, ethyl chrysanthemumate, o-anisaldehyde, 4-tert-butylcyclohexyl acetate, 4-hydroxybenzaldehyde, 1-fenchone, pyrazine, pinacol, 2-methoxynaphthalalene, cis-3-hexenylacetate, 3'4'-dimethoxy acetophenone compounds. The vanilla fragrance can be formulated by using acetanisole, anisyl acetate, anisyl alcohol, anisyl propionate, benzoin, cinnamaldehyde, ethyl vanillin, 2-methoxy-4-methylphenol, 1-(p-methoxyphenyl)-2-propanone, propenyl guaethol, vanillin, veratraldehyde, vanillylacetone, vanillin isobutyrate, veratrole, acetovanillone compounds.

The camphoraceous catagory of the fragrance includes the following compounds: isoborneol, (+)-camphene, d-camphor, 1-dihydrocarvyl acetate, eucalyptol, 4-methylanisole, (r)-(+)-pulegone, 2-sec-butylcyclohexanone, myrtenal, (1r)-(−)-myrtenol, 2-ethylfenchol, trithioacetone, 1,4-cineole, theaspirane, butyrophenone, (is)-(−)-verbenone, and 1-fenchone.

The chemical category of the fragrances include the following compounds: amyl alcohol, isobornyl propionate, butyl alcohol, butylated hydroxytoluene, 4-allylanisole, heptyl alcohol, mycrene, isopentylamine, phenethylamine, 4-methyl-3-penten-2-one, 3-methyl-2-cyclopenten-1-one, and 2,6-dimethyl-4-heptanone.

The citrus category includes lemon, lime, orange etc. The lemon fragrances can be formulated by using α-amyclinnamaldehyde dimethyl acetal, citral dimethyl acetal, fencyl alcohol, undecyl alcohol, α-terpinene compounds. The lime fragrances can be formulated by using undecyl alcohol compound. The orange fragrances can be formulated by using decyl acetate, dimethyl anthranilate, neryl butyrate, neryl isobutyrate, octyl formate, undecanal, undecyl alcohol, trans-2-pentenal, cis-4-decenal, 2-undecenal compounds. The remaining citrus catatory fragrances can be formulated by using benzyl alcohol, citral diethyl acetal, p-cymene, decanal, decanoic acid, 2-decenal, decyl butyrate, heptyl acetate, heptyl alcohol, lauryl acetate, (r)-(+)-limonene, linalool, linalyl formate, methyl octanoate, myristaldehyde, nerolidol, nonanal, nonyl alcohol, 1-octanol, octyl butyrate, terpinyl formate, 2-tridecenal, 2-undecanone, 10-undecenal, trans,trans-2,4-decandienal, ethyl-3-(methylthio)propionate, 2,4-hexadienal, ethyl-3-hydroxyhexanoate, γ-terpinene, cis-6-nonenal, 3-decanone, dimethylmaleate compounds.

The coffee catagory of the fragrances can be formulated by using 2-methylbutyraldehyde, methyl cyclopentenolone, 2-thiophenethiol, 2-ethyl-3,5(or 6)-dimethylpyrazine, 3-ethyl-2-hydroxy-2-cyclopenten-1-one, furfuryl methyl sulfide, furfuryl isopropyl sulfide, 2-furyl methyl ketone, 2-methyl-3-furanthiol, 5-methylquinoxaline, 2,3,5,6-tetramethylpyrazine, 2,2'(thiodimethylene)difuran, 3,5-dimethyl-1,2-cyclopentadione, 2,3-dimethylpyrazine, 2,6-dimethylpyrazine, ethyl thioacetate, 2,4,5-trimethylthiazole, allyl thiopropionate, furfuryl thiopropionate, methyl furfuryl disulfide, 2,6-dimethylpyridine, 2-ethylfuran, ethyl3-(furfurylthio)propionate, and 2,4-dimethylthiazole.

The earthy category of the fragrances can be formulated by using amyl formate, 4-carvomethenol, m-dimethoxybenzene, lauryl alcohol, 2-methylanisole, α-methylanisole, α-methylbenzyl pripionate, 2-octanol, 1-octen-3-ol, octyl isobutyrate, hydrocinnamaldehyde, 2-phenylpropionaldehyde dimethyl acetal, 1-phenyl-2-pentanol, tetrahydrofurfuryl propionate, 2,3-diethylpyrazine, 3-ethyl-2-methylpyrazine, 1-methylnaphthalene, phenyl disulfide, 1-furfurylprrole, 2-heptanol, 3-hexanone, 5(h)-5-methyl-6,7-dihydrocyclopenta-(b)pyrazine, 2-methoxy-3(5 or 6)-isopropylpyrazine, 2-methylpentanal, trithioacetone, 2-ethylfenchol, 3,5,5-trimethylhexanal, 2-isopropyl-4-methylthiazole, 2-methyl-3(5 or 6)-ethoxypyrazine, benzyl disulfide, 2-methyl-3-buten-2-ol, amyl acetate compounds.

The ethereal category of the fragrances can be formulated by using acetaldehyde, acetaldehyde, 5 wt % solution in ethanol, acetaldehyde phenethyl propyl acetal, amyl formate, 2-butanone, isobutyl acetate, isobutyl butyrate, isobutyl isobutyrate, isobutyl formate, butyl propionate, butyl valerate, butyl isovalerate, butyraldehyde, decyl propionate, ethyl acetate, ethyl acetoacetate, ethyl butyrate, ethyl formate, ethyl levulinate, ethyl 3-phenylpropionate, ethyl propionate, ethyl sorbate, 3-heptanone, hexyl formate, methyl acetate, methyl butyrate, ethyl hexanoate, 4-methyl-2-pentanone, neryl isovalerate, 2-pentanone, propyl formate, isopropyl phenylacetate, 3-hexanone, acetone, 3-hexanol, 4-hexen-3-one, pyrrole, 2-methylpentanal, ethyl trans-2-butenoate, methyl-3-hydroxyhexanoate, m-cresol, 2,6-dimethyl-4-heptanone, 2-ethylfuran, methyl tiglate, amyl acetate, ethyl chrysanthemumate compounds.

The fatty category of the fragrances is subdivided as butter, cheese creamy oily, sour etc. The butter fragrances can be formulated by incorporating acetanisole, acetoin, anisole, benzyl butyrate, butyl butyryllactate, isobutyric acid, δ-decalactone, diacetyl, δ-dodecalactone, ethyl lactate, 2,3-hexanedione, 2-methylheptanoic acid, 3-octanone, 2,3-pentanedione, 3,4-hexanedione, δ-nonalactone, cis-3-hexenyl butyrate, 2-acetoxy-3-butanone, 1-penten-2-ol, 3-methyl-2-butenal, 5-(hydroxymethyl)furfural compounds.

The cheese fragrances can be formulated by incorporating anisole, benzyl benzoate, benzyl butyrate, butyl butyryllactate, butyric acid, hexanoic acid, 2-methylbutyric acid, 2-methylheptanoic acid, 2-methylpentanoic acid, nonanoic acid, 4-pentenoic acid, propyl hexanoate, tetrahydrofurfuryl butyrate, isovaleric acid, methyl thiobutyrate, 5,6,7,8-tetrahydroquinoxaline, butan-3-one-2-yl butyrate, 4-methylpentanoic acid compounds.

The creamy fragrances can be formulated by incorporating acetoin, butyl lactate, tributyrin, 2,3-hexanedione, methylp-tert-butylphenylacetate, 2-methylheptanoic acid, methyl laurate, γ-octalactone, octyl isobutyrate, cis-4-heptenal, methyl 2-thiofuroate, 3-methylpentanoic acid, 2-acetoxy-3-butanone, methyl cyclohexanecarboxylate, 2-oxobutyric acid, veratrole, 4-tert-butylcyclohexylacetate compounds.

The oily fragrances can be formulated by incorporating 3-methyl-1-butanol, amyl 2-furoate, butyl laurate, citral diethyl acetal, cuminaldehyde, diacetyl, 2-ethylbutyl acetate, ethyl decanoate, farnesol, furfuryl mercaptan, heptanal, heptyl acetate, heptyl alcohol, 2,3-hexanedione, 6-methyl-5-hepten-2-one, myristic acid, octanoic acid, 2-octanol, propyl propionate, 2-ethyl-1-hexanol, trimethylamine, undecanoic acid, 2-acetylpyridine, 2-heptanol, α-angelicalactone, 2-pentanol, 3, 5, 5-trimethyl-1-hexanol, methyl 3-hydroxyhexanoate, perillaldehyde, 3-octanol, 3-methyl-2-butenal, isopropyl 2-methylbutyrate, 2-methyl-3-buten-2-ol, methyl stearate, methyl decanoate.

The sour and other fragrances can be formulated by incorporating 2-ethylbutyric acid, isovaleraldehyde, phenoxyacetic acid, heptanoic acid, allyl hexanoate, allyl octanoate, butyl stearate, decanoic acid, decyl butyrate, p-dimethoxybenzene, γ-dodecalactone, ethyl 10-undecenoate, heptanal, 3-heptanone, heptyl formate, hexanal, hexyl 2-furoate, lauric acid, lauryl alcohol, perillyl alcohol, methyl myristate, 2-methylundecanal, nonanal, 2-nonanone, oleic acid, propyl heptanoate, undecanal, trans, trans-2,4-decadienal, 3,7-dimethyl-6-octenoic acid, 2,4-heptadienal, trans-2-hexenoic acid, trans,trans-2,4-nonadienal, 2-nonenal, 2-acetylpyridine, 2-nonanol, 3-methyl-2-cyclopenten-1-one, 1,6-hexanedithiol, cyclohexanecarboxylic acid, 4-methyloctanoic acid, trans-2,trans-4-octadienal, furfuryl hexanoate, methyl(p-tolyloxy)acetate, trans-3-hexen-1-ol compounds.

The floral category of the fragrances is subdivided as blossom, carnation, gardenia, geranium, hawthorne, hyacinth, iris, jasmin, jonquil, lilac, lilly, marigold, narcissus, rose, violet etc. The compounds used to formulate these fragrances include dimethylanthranilate, methylβ-naphthyl ketone, neryl acetate, 2-methoxynaphthalene; phenethyl salicylate, 5-phenyl-1-pentanol; α-methylbenzyl acetate, α-methylbenzyl propionate, geranyl tiglate; isopulegol, biphenyl, diphenyl ether; acetophenone, p-anisaldehyde, 4'-methylacetophenone, 2'-hydroxyacetophenone; anisyl alcohol, cinnamyl alcohol, α-methylbenzyl alcohol, methylp-tert-butylphenylacetate, methyl2-methoxybenzoate, phenethyl salicylate, phenylacetaldehyde dimethyl acetal, 3-phenyl-1-propanol, hydrocinnamaldehyde, p-tolyl phenylacetate; phenethylanthranilate; α-amylcinnamaldehyde, α-amylcinnamaldehyde dimethyl acetal, benzyl acetate, benzyl butyrate, benzyl isobutyrate, benzyl propionate, cyclohexaneacetic acid, ethyl2-acetyl-3-phenylpropionate, α-hexylcinnamaldehyde, methylp-tert-butylphenylacetate, methyl phenylacetate, octyl acetate, cis-jasmone, 3-decen-2-one; p-tolyl phenylacetate; anisyl acetate, α-terpineol; α-amylcinnamaldehyde dimethyl acetal, p-tolyl isobutyrate, p-tolyl phenylacetate; butyl heptanoate; p-tolyl isobutyrate compounds.

The rose fragrances can be formulated by incorporating butyl phenylacetate, cinnamyl isovalerate, citronellyl butyrate, citronelly valerate, 1-cecanol, 3,7-dimethyl-1-octanol, geraniol, geranyl acetate, lauryl acetate, methylp-tert-butylphenylacetate, nerolidol, neryl acetate, neryl isobutyrate, nonanal, nonyl alcohol, octyl formate, octyl isovalerate, phenethyl acetate, phenethyl alcohol, phenthyl benzoate, phenthyl isobutyrate, phenethyl salicylate, phenethyl tiglate, phenethyl isovalerate, 2-phenoxyethyl isobutyrate, 3-phenylpropionic acid, propyl phenylacetate, isopropyl phenylacetate, undecaal, 2-undecanone, 10-undecenal, 2-ethyl-1-hexanol, phenthyl hexanoate, 5-phenyl-1-pentanol, citronellyl tiglate compounds.

The violet and other fragrances can be formulated by incorporating ethyl-2-nonynoate, α-lonone, methyl 2-nonenoate, methyl 2-nonynoate, methyl 2-octynoate, trans-2,cis-6-nonadienal, allyl α-ionone, isoamyl nonanoate, anisyl formate, anisyl propionate, benzaldehyde dimethyl acetal, benzyl acetoacetate, benzyl cinnamate, isobornyl propionate, cinnamyl acetate, cinnamyl butyrate, 2',4'-dimethylacetophenone, ethyl benzoate, ethyl salicylate, farnesol, geranyl acetate, 1-hexadecanol, β-ionone, lauric aldehyde, linalool, 4-(p-methoxypenyl)-2-butanone, methyl isobutyrate, 2-methylanisole, 4-3,4-methylendioxyphenyl)-2-butanone, methyl 3-phenylpropionate, neryl butyrate, neryl isobutyrate, 2-nonanone, 2-octanone, phenthyl butyrate, benzylideneacetone, 2-phenylpropionaldehyde, 2-phenylpropyl isobutyrate, piperidine, piperonal, p-isopropylbenzyl alcohol, 3-propylidenephthalide, terpinyl formate, vanillin acetate, o-methoxycinnamaldehde, trans, trans-2-4-nonadienal, phenethyl octanoate, furfuryl propionate, phenethyl 2-methylbutyrate, isoeugenyl benzyl ether, dihydrojasmone, ethyl 2-furoate, phtol, 3-decanone, o-anisaldehyde, 3',4'-dimethoxyacetophenone compounds.

The fruity category of the fragrances is subdivided as apple, apricot, banana, berry, cherry, coconut, grape, grapefruit, jam, melon, peach, pear, pineapple,plum, quince, raspberry, strawberry etc. The apple fragrances can be formulated by incorporating isoamyl hexanoate, isoamyl isovalerate, benzyl acetate, benzyl isovalerate, isobutyl acetate, butyl butyrate, butyl isobutyrate, butyl heptanoate, isobutyl hexanoate, butyl valerate, butyl isovalerate, cyclohexyl butyrate, ethyl hexanoate, ethyl levulinate, ethyl 2-methybutyrate, ethyl valerate, ethyl isovalerate, isoeugenyl phenylacetate, geraniol, heptyl formate, trans-2-hexenal, hexyl acetate, linalyl isovalerate, 2-methoxy-4-vinylphenol, α-methylbenzyl acetate, methyl 2-methylbutyrate, methyl propionate, methyl isovalerate, nerolidol, neryl acetate, phenethyl acetate, trans-2-pentenal, acetone, 2-methylbutyl 2-methylbutyrate, cis-3-hexenyl 2-methylbutanoate, 3-hexenyl 3-methylbutanoate, hexyl 3-methylbutanoate, 2-methylbutyl isovalerate, 3-octyl acetate, propyl tiglate compounds.

The apricot fragrances can be formulated by incorporating allyl butyrate, allyl heptanoate, isoamyl butyrate, isoamyl nonanoate, isoamyl propionate, benzophenone, benzyl acetate, benzyl butyrate, benzyl cinnamate, ethyl octanoate, ethyl phenylacetate, geraniol, heptyl acetate, hexyl butyrate, α-methylbenzyl acetate, phenethyl acetate, phenylacetaldehyde, 2-phenylpropyl butyrate, propyl phenylacetate, pentyl 2-furyl ketone, isoamyl isobutyrate compounds.

The banana fragrances can be formulated by incorporating allyl heptanoate, allyl octanoate, isoamyl acetate, amyl butyrate, isoamyl butyrate, isobutyl acetate, amyl butyrate, isoamyl butyrate, isobutyl acetate, butyl butyrate, butyl isobutyrate, butyl propionate, isobutyraldehyde, cyclohexyl propionate, ethyl benzoae, ethyl butyrate, ethyl hexanoate, furfuryl acetate, 2-heptanone, methyl propionate, isopropyl acetate, phenethyl hexanoate, ethyl 2-methyl-4-pentanoate, 2-methylbutyl acetate, amyl acetate, prenyl acetate, diethyl maleate. The berry fragrances can be formulated by incorporating allyl heptanoate, allyl tiglate, benzyl alcohol, benzyl butyrate, benzyl propionate, butyl butyrate, 2-ethylbutyric acid, ethyl heptanoate, geraniol, dl-menthyl acetate, methyl 2-furoate, methyl heptanoate, ω-pentadecalactone, phenylacetaldehyde, piperonyl isobutyrate, propyl formate, p-mentha-8-thiol-3-one, furfuryl 3-methylbutanoate, butan-3-one-2-ylbutyrate, 2-methylbutyl 2-methylbutyrate, 2-isopropyl-5-methyl-2-hexenal, 3-methylpentanoic acid, dicyclohexyl disulfide, methyl cyclohexanecarboxylate, 4-(p-acetoxyphenyl)-2-butanone, ethyl 3-oxohexanoate, o-tolyl isobutyrate compounds.

The cherry fragrances can be formulated by incorporating amyl butyrate, benzyl acetate, benzyl alcohol, benzyl benzoate, benzyl cinnamate, ethyl benzoate, ethyl phenylacetate, hexyl acetate, α-lonone, 4-(p-methoxyphenyl)-2-butanone, hydrocinnamaldehyde, piperonal, piperonyl acetate, 3-methyl-2-cyclohexene-1-one, 2,4-dimethylbenzaldehyde, perillaldehyde, butyrophenone compounds.

The coconut fragrances can be formulated by incorporating δ-decalactone, m-dimethoxybenzene, δ-dodecalactone, γ-heptalactone, lauryl alcohol, 6-methylcoumarin, methyl laurate, methyl nonanoate, γ-nonalactone, γ-octalactone, ethyl undecanoate, 6-amyl-α-pyrone, whiskey lactone compounds.

The grape fragrances can be formulated by incorporating isobutyl isobutyrate, ethyl anthranilate, ethyl decanoate, methyl anthranilate, dimethyl anthranilate, phenethyl butyrate, hexyl isobutyrate, 3-hexanone, acetone, ethyl-3-hydroxybutyrate, isoamyl isobutyrate, ethyl-3-hydroxyhexanoate, furfuryl butyrate compounds.

The grapefruit fragrances can be formulated by incorporating benzyl alcohol, 2-,3-, and 10-mercaptopinane compounds, whereas jam fragrances fragrances can be formulated by incorporating allyl tiglate, piperonyl isobutyrate, mytenal, 4-(p-acetoxypenyl)2-butanone compounds.

The melon fragrances can be formulated by incorporating 2,6-dimethyl-5-heptenal, ethyl heptanoate, 2-nonanol, cis- 6-nonen-1-ol, cis-6-nonenal, methyl 3-nonenoate compounds, whereas the peach fragrances can be formulated by incorporating allyl butyrate, allyl cinnamate, benzophenone, benzyl butyrate, benzyl cinnamate, butyl butyrate, butyl isovalerate, γ-decalactone, δ-decalactone, δ-dodecalactone, ethyl cyclohexanepropionate, ethyl heptanoate, isovaleraldehyde, methyl 2-nonynoate, γ-undecalactone, δ-undecalactone, furfuryl octanoate, pentyl-2-furyl ketone compounds.

The pear fragrances can be formulated by incorporating isoamyl acetate, benzyl butyrate, butyl butyrate, ethyl cyclohexanepropionate, ethyl decanoate, heptyl acetate, hexyl acetate, hexyl propionate, linalyl acetate, linalyl propionate, isopropyl isobutyrate, ethyl trans-2, cis-4-decadienoate, acetone, cis-3-hexenyl hexanoate compounds.

The pineapple fragrances can be formulated by incorporating allyl cyclohexanepropionate, allyl heptanoate, allyl hexanoate, allyl octanoate, allyl phenoxyacetate, amyl butyrate, isoamyl butyrate, isoamyl hexanoate, isoamyl propionate, benzyl benzoate, benzyl cinnamate, benzl isovalerate, cyclohexyl butyrate, cyclohexyl propionate, decyl acetate, ethyl acetate, ethyl butyrate, ethyl 3-(2-furyl) propanoate, ethyl heptanoate, ethyl hexanoate, ethyl levulinate, ethyl octanoate, ethyl propionate, 4-heptanone, hexyl butyrate, α-methylbenzylacetate, methylhexanoate, methyl 4-methylvalerate, propyl isobutyrate, isopropyl isobutyrate, phenethyl hexanoate, acetone, ethyl trans-3hexenoate, ethyl 3-(methylthio)propionate, hexyl trans-2-butenoate, ethyl 2-methylpentanoate, ethyl 2-methyl-4-pentenoate, isoamyl isobutyrate, ethyl 3-hydroxyhexanoate compounds.

The plum fragrances can be formulated by incorporating isoamyl formate, anisyl acetate, benzyl acetate, benzyl butyrate, butyl anthranilate, butyl formate, ethyl benzoate, ethyl cinnamate, ethyl heptanoate, ethyl 2-methylbutyrate, heptyl formate, trans-2-hexenal, α-methylbenzylacetate, hydrocinnamaldehyse, 3-phenylpropylisovalerate, triethyl citrate, ethyl 2-furoate, whereas quince fragrances can be formulated by incorporating diethyl sebacate compound.

The raspberry fragrances can be formulated by incorporating butyl valerate, ethyl tiglate, 4-(p-methoxyphenyl)-2-butanone, α-Ionone, 4-(p-methoxyphenyl) -2-butanone, 3-phenylpropylisovalerate compounds, whereas the strawberry fragrances can be formulated by incorporating benzyl benzoate, ethyl isobutyrate, ethyl 3-methyl-3-phenylglycidate, ethyl(±)-3-phenylglycidate, methycinnamate, methyl propionate, phenethyl butyrate, 3-phenylpropylisovalerate, piperonyl acetate, 4-hydroxy-2,5-dimethyl-3(2h)-furanone, maltylisobutyrate, hexyl 3-methylbutanoate compounds.

The remaining fruity fragrances can be formulated by incorporating acetanisole, allylα-ionone, allyl nonanoate, amyl formate, anisyl alcohol, anisyl propionate, benzyl acetoacetate, benzyl isobutyrate, isobutyl acetoacetate, isobutyl alcohol, isobutyl butyrate, isobutyl cinnamate, isobutyl formate, butyl hexanoate, butyl levulinate, butyraldehyde, cinnamyl butyrate, cinnamyl isobutyrate, cinnamyl propionate, citronellyl butyrate, cyclohexane ethyl acetate, cyclohexyl acetate, cyclohexyl isovalerate, 1-decanol, decyl propionate, benzyl ether, diethyl malate, diethyl malonate, diethyl-tartrate, dimethyl succinate, γ-dodecalactone, ethyl 2-acetyl-3-phenylpropionate, ethyl acrylate, ethylp-anisate, 2-ethylbutyl acetate, ethyl formate, ethyl lactate, ethyl laurate, ethyl nononoate, ethyl-3-phenylpropionate, ethyl salicylate, ethyl sorbate, ethyl 10-undecenoate, 3-heptanone, trans-2-hexen-1-ol, 4'-methylacetophenone, methyl benzoate, α-methylbenzyl butyrate, methyl isobutyrate, 2-methylbutyric acid, methyl 3-(methylthio)propionate, 4-methyl-2-pentanone, methyl 3-phenylpropionate, methyl valerate, myristaldehyde, 2-nonanone, 2-octanone, octyl acetate, 2-pentanone, phenthyl anthranilate, phenthyl isobutyrate, phenethyl isovalerate, 2-phenylpropyl isobutyrate, 3-phenylpropyl isobutyrate, isopropyl butyrate, propyl heptanoate, propyl propionate, tetrahydrofurfuryl butyrate, tetrahydrofurfuryl propionate, cis-3-hexenyl acetate, 2-methyl-2-pentenal, trans-2-methyl-2-pentenoic acid, cis-jasmone, phenethyl octanoate, ethyl 2-mercaptopropionate, 3-(5-methyl-2-furyl) butanal, ethyltrans-3-hexe.noate, 4-(methylthio)-2-butanone, butyl 2-methylbutyrate, furfuryl pentanoate, 2-methyl-2-butenal, 2-methylpentanal, 3-penten-2-one, isobutyl trans-2-butenoate, 3-methyl-2-cyclopenten-1-one, 3-nonanone, hexyl 2-methylbutanoate, methyl 3-hydroxyhexanoate, cyclohexanecarboxylic acid3-decen-2-one, 2,6-dimethyl-4-heptanone, phenethyl 2-methylbutyrate, δ-cyclocitral, 3-methyl-2-buten-1-ol, isopropyl 2-methylbutyrate, methyl trans-2-octenoate, dihydrojasmone, citronellyl tiglate, geranyl tiglate, hexyl tiglate, isoamyl tiglate, methyl decanoate, methyl (p-tolyloxy)acetate, phenyl salicylate, 3-methyl-3-pentanol, ethyl (±)-2-hydroxycaproate compounds.

The green fragrances can be formulated by incorporating acetalehyde phenethyl propyl acetal, allyl disulfide, allyl sulfide, allyl tiglate, α-amylcinnamaldehyde dimethyl acetal, isoamyl hexanoate, isoamyl sallicylate, butyl sulfide, (−)-carvyl acetate, cinnamyl formate, citral diethyl acetal, cyclohexyl isovalerate, 4-allylanisole, ethyl3-(2-furyl) propanoate, ethyl laurate, ethyl 2-methylbutyrate, ethyl 2-nonynoate, ethyl pyruvate, 3-heptanone, heptyl butyrate, hexanal, trans-2-hexenal, trans-2-hexen-1-ol, cis-3-hexen-1-ol, hexyl alcohol, hexyl formate, hexyl 2-furoate, hexyl hexanoate, hexyl octanoate, hexyl propionate, linalyl formate, perilly alcohol, α-methylbenzyl acetate, α-methylbenzyl propionate, methylp-tert-butylphenylacetate, methyl heptanoate, 6-methyl-5-hepten-2-one, methyl 2-nonenoate, methyl octanoate, methyl 2-octynoate, nerolidol, neryl butyrate, trans-2, cis-6-nonadien-1-ol, 2-octanone, octyl butyrate, octyl isobutyrate, phenylacetaldehyde dimethylacetal, phenylacetic acid, propyl formate, propyl heptanoate, 1-phenyl-2-pentanol, undecyl alcohol, biphenyl, 2-isobutyl-3-methoxypyrazine, 2-isobutylthiazole, trans-2-heptenal, cis-3-hexenyl acetate, 3-methylcrotonic acid, 2-methyl-2-pentenal, trans-2-octenal, trans-2-pentenal, phenethyl hexanoate, phenethyl octanoate, propyl disulfide, 2,3-dimethylpyrazine, 1-furfurylpyrrole, 2-nonanol, 2-pentanol, 2-pentylfuran, cis-3-hexenyl formate, 2-methoxy-3(5 or 6)-isopropylpyrazine, 2-(1-methylpropyl) thiazole, trans-2, cis-6-nonadienal, cis-3-hexenyl butyrate, cis-3-hexenyl hexanoate, trans-2methyl-2-butenal, 2,4-hexadienal, 2-methoxy-3-(1-methylpropyl) pyrazine, 3-(methylthio)-1-hexanol, dicyclohexyl disulfide, hexyl phenylacetate, cis-6-nonen-1-ol, ethyl 2-methyl-4-pentenoate, 3-hexenyl 3-methylbutanoate, hexyl2-methylbutanoate, 2,6-dimethylpyridine, 2-isopropyl-4-methylthiazole, perillaldehyde, 4-methyloctanoic acid, 1-penten-3-ol, benzyl disulfide, δ-cyclocitral, 3-methyl-2-buten-1-01, diphenyl ether, 2-ethyl-4-methylthiazole, ethyl 3-oxohexanoate, cis-3-hexenylbenzoate, methyltrans-2-octenoate, 4-methylthiazole, trans-2,trans-4-octadienal, 3-methyl-1-pentanol, dihydrojasmone, trans,trans-2,6-nonadienal, theaspirane, hexyl tiglate, propyl tiglate, cis-3-hexenyl tiglate, furfuryl hexanoate, furfuryl heptanoate, whiskey lactone, prenyl acetate, trans-3-hexen-1-ol, trans, trans-2,4,hexadien-1-ol, 3-methyl-3-pentanol, cis-3-hexenyl salicylate, ethyl(±)-2-hydroxycaproate compounds.

The herbaceous fragrance category is subdivided as caraway, sage etc. These fragrances can be formulated by incorporating /-carveol; linayl isovalerate, neryl isovalerate; acetaldehyde phenethyl propyl acetal, benzyl isovalerate, isobornyl propionate, butyl heptanoate, butyl sulfide, /-carvone, cinnamyl formate, citronellyl valerate, dihydrocoumarin, 4-allylanisole, γ-heptalactone, γ-hexalactone, hexyl alcohol, hexyl hexanoate, lauric aldehyde, linalyl formate, linayl propionate, 6-methylcoumarin, 6-methyl-5-hepten-2-one, methyl 2-methoxybenzoate, 2-methylundecanal, 2-nonanone, γ-octalactone, 2-octalactone, 2-octanone, 3-octanone, 1-octen-3-ol, α-phellandrene, phenethyl tiglate, isopulegol, (r)-(+)-pulegone, isoquinoline, tributyl acetylcitrate, γ-valerolactone, trans-2-octenal, propyl disulfide, 3,4-dimethyl-1,2-cyclopentadione, 3,5, 5-trimethyl-1-hexanol, 3-butylidenephthalide, 2-(1-methylpropyl) thiazole, 2-tridecanone, safranal, 3-methylpentanoic acid, 3-nonanone, cis-3-hexenyl 2-methylbutanoate, 3-heptanol, 2'-hydroxyacetophenone, -terpinene, d-dihydrocarvone, 3-octanol, cis-3-hexenyl benzoate, methyl nicotinate, myrtenyl acetate, isobutyl liglate, 2-methyl-3-buten-2-ol, ethyl chrysanthemumate, trans, trans-2,4-hexadien-1-ol, 1-methylpyrrole compounds.

The meaty category of the fragrance can be formulated by incorporating allylα-ionone, benzyl mercaptan, butyraldehyde, 4-ethylgualacol, guaiacyl phenylacetate, 3-(methylthio)priopionaldehyde, butylamine, 2,3-diethylpyrazine, 2,6-dimethoxypenol, 2,2'-(dithiodimethylene)difuran, furfuryl isopropyl sulfide, 2,-mercaptopropionic acid, 4-methyl-5-thiazoleethanol, 4-methyl-5-thiazoleethanol acetate, pyrazineethanethiol, 2,2'-(thiodimethylene)difuran, o-toluenethiol, trimethylamine, 2-acetyl-3-ethylpyrazine, cyclopentanethiol, 4,5-dihydro-3(2h)thiophenone, 2,4-dimethyl-5-acethylthiazole, 2,3-dimethylpyrazine, 2,5-dimethylpyrazine, 2,6-dimethylpyrazine, 4,5-dimethylthiazole, dimethyl trisulfide, 2-methylpyrazine, 2-naphthalenethiol, 2-acetylthiazole, 2-ethoxythiazole, 3-acetyl-2,5-dimethylfuran, 1,6-hexanedithiol, 1,9-nonanedithiol, 1,8-octanedithiol, 3-acetyl-2,5-dimethylthiophene, 2-isopropyl-4-methylthiazole, 1,3-propanedithiol, 4-allyl-2,6-dimethoxyphenol, ethyl 3-(furfurylthio)propionate, ethyl 3-mercaptopropionate, 2,4-dimethylthiazole, d-camphor, p-cresol, /-dihydrocarvylacetate, guaiacol, propenyl guaethol, tetrahydrofurfuryl propionate, thymol, p-ethylphenol, 1-phenyl-1,2-propanedione, styrene, 2,6-xylenol, 2,5-dimethylpyrazine, 3-hexanol, 3-methyl-2-cyclohexen-1-one, (1r)-(−)mytenol, 2-isopropylphenol, o-cresol, m-cresol, 2,5-xylenol, 5-phenyl-1-pentanol, 4-propylphenol, o-tolyl isobutyrate, propylene carbonate, 4-isopropylphenol, 3,4-dihydroxybenzaldehyde compounds.

The minty category of the fragrance can be formulated by incorporating /-carveol, /-carvone, (−)-carvyl acetate, (−) carvyl propionate, dihydrocarveol, /-dihydrocarvyl acetate, 4-allylanisole, ethyl salicylate, dl-methyl acetate, methyl salicylate, α-phellandrene, isopulegol, (r)-(=)-pulegone, isopulegly acetate, isopropyl tiglate, 4, 5, 6, 7-tetrahydro-3, 6-dimethylbenzofuran, (1r)-(−)-myrtenol, d-dihydrocarvone, 3-octyl acetate, δ-cyclocitral, /-menthyl lactate, menthalactone, theaspirane, propylene carbonate, (1s)-(−)-verbenone compounds.

The mossy category of the fragrance can be formulated by incorporating 4-methyloctanoic acid, 2,5-dimethyl-4-methoxy-3(2h)furanone, ethyl 3-oxohexanoate compounds, whereas musty catagory of the fragrance can be formulated by incorporating butylated hydroxytoluene, 4-carvomenthenol, ethyl 10-undecenoate, hexyl 2-furoate, hexyl propionate, indole, α-methylbenzyl propionate, octyl butyrate, phenethyl2-furoate, γ-undecalactone, trans-2-hexenoic acid, 4, 5, 6, 7-tetrahydro-3,6-dimethybenzofuran, 2, 3, 5, 6-tetramethylpyrazine, 2-sec-butycyclohexanone, 2-ethylpyrazine, furfuryl pentanoate, 4-oxoisophorone, dicyclohexyl disulfide, o-cresol, 4-methyloctanoic acid, 2-methoxyphenyl acetate, 5-(hydroxymethyl)fufural, furfuryl hexanoate compounds.

The nutty category of the fragrance can be subdivided as almond, hazelnut, peanut, walnut etc. The almond fragrances can be formulated by incorporating acetophenone, benzaldephyde, benzyl benzoate, benzyl ether, dihydrocoumarin, furfural, trans-2-hexenal, 5-methylfurfural, 3,4-hexanedione, 2-methoxy-3-methylpyrazine, 2,3-dimethylpyrazine, 2,4-dimethylbenzaldehyde, 2-methyl-2(5 or 6)-ethoxypyrazine, 6-amyl-α-pyrone, 4-ethylbenzaldehyde compounds.

The hazelnut fragrance can be formulated by incorporating 2,3-diethlpyrazine, 3-ethyl-2-methlpyrazine, 2,4-heptadienal, 2-methoxy-3-methylpyrazine, 2, 3, 5-trimethylpyrazine, 2, 4, 5-trimethylthiazole, 2-acetyl-3,5 (or 6)-dimethylpyrazine, 2-acetylthiazole, 2,3-diethyl-5-methylpyrazine, 2-methyl-3(5 or 6)-ethoxypyrazine compounds.

The peanut fragrances can be formulated by incorporating 2-methoxy-4-vinylphenol, 2-methoxy-3-methylpyrazine compounds, while walnut fragrance can be formulated by incorporating benzyl alcohol, 2-methylanisole, 2-phenylpropionaldehyde dimethyl acetal, 2,3-dimethylpyrazine, 2-methoxyphenyl acetate. Other compounds used for formulating nutty fragrances include acetanisole, benalehyde dimethyl acetal, methyl nonanoate, methyl valerate, phenylacetaldehyde, valeraldehyde, 2-acetylpyrazine, 2-ethyl-3,5(or6)-dimethylpyrazine, 5-methylquionoxaline, 4-methyl-5-tiazoleethanol, 2-acetyl-3-ethylpyrazine, 2,5-dimethylpyrazine, 2,6-dimethylpyrazine, 4,5-dimethylthiazole, 2-ethylpyrazine, α-angelicalactone, 2-methoxypyrazine, 2-methylpyrazine, 4-methyl-5-vinylthiazole, 2-ethoxythiazole, pyrrole, 3-acetyl-2,5-dimethylfuran, 2-heptylfuran, 3-acetylpyridine, 2,6-dimethylpyridine, 2-isopropyl-4-methylthiazole, 3-octanol, 2-acetyl-5-methylfuran, thiazole, 2-ethyl-4-methylthiazole, 4-methylthiazole, 2-acetyl-3-methylpyrazine, 2-methyl-3-propylpyrazine compounds.

The smoky category of the fragrances can be formulated by incorporating 4-ethylguaiacol, furfuryl mercaptan, guaiacol, guaiacyl phenylacetate, methyl cyclopentenolone, 2,6-dimethoxyphenol, 3,7-dimethyl-6-octenoic acid, 3-ethyl-2-hydroxy-2-cyclopenten-1-one, 3-ethylpyridine, ethyl 3-hydroxyhexanoate, d-xylose, benzyl disulfide, 1-methylpyrrole compounds.

The spicy category of the fragrances can be formulated by incorporating allyα-ionone, β-caryophyllen, cinnameldeyde, cinnamic acid, cinamyl propionate, cinnamyl isovalerate, benzyl ether, p-ethoxybenzaldehyde, ethyl cinnamate, eugenol, methyl eugenol, isoeugenyl phenylacetate, methyl isoeugenol, 3-(2-fury)acrolein, 2-heptanone, 2-methoxy-4-vinylphenol, α-methylcinnamaldehyde, 5-methylfurfural, 4-methyl-2-pentanone, 4-methyl-1-phenyl-2-pentanone, methyl salicylate, 3-octanone, 2-phenylpropionaldehyde dimethyl acetal, salicylaldehyde, vanillylacetone, o-methoxycinnamaldehyde, trans-2-octenal, furfuryl propionate, 2-tridecanone, 2,4-dimethylbenzaldehyde, 2-methoxy-4-propylphenol, trans-2-methyl-2-butenoic acid, 1,4-cineole, 1-ethylhexyl tiglate, isoeugenol benzyl ether, propylene carbonate, 4-isopropylphenol, (1s)-(−)-verbenone compounds.

The sulfurous category of the fragrances can be formulated by incorporating ammonium sulfide, methyl sulfide, methyl sulfide, redistilled, phenyl disulfide, pyrazineethanethiol, methyl 2-thiofuroate, trithioacetone, propyl mercaptan, 2,6-dimethylthiophenol compounds.

The vegetable category of the fragrances can be formulated by incorporating hexyl octanoate, methy 2-octynoate, methyl sulfide, trans-2, cis-6-nonadien-1 ol, tetrahydrofurfuryl alcohol, 1-furfurylpyrrole, 3-(5-methyl-2-furyl) butanol, 2-pentylfuran, cis-3-hexenyl formate, 2-methoxy-3(5 or 6)-isopropylpyrazine, 2,3-diethyl-5-methylpyrazine, methyl furfuryl disulfide, 4-methyl-3-pentan-2-one, propyl mercaptan, trans-2,4-octadienal, trans, trans-2,6-nonadienal, allyl cyclohexanepropionate, allyl nonanoate, isoamyl laurate, myristic acid, decanl, 1-decanol, 2-decenal, decyl butyrate, ethyl myristate, ethyl palmitate, ethyl phenylacetate, ethyl 10-undecenoate, 1-hexadecanol, lauric aldehyde, lauryl alcohol, methyl laurate, nonanal, nonanoic acid, 2-tridecenal, 10-undecenal, 2-nonenal, trans-2,cis-6-nonadienal, ethyl stearate, octyl 2-furoate, furfuryl hexanoate compounds.

The wine-like category of the fragrances can be formulated by incorporating allyl nonanoate, amyl octanoate, isobutyl acetoacetate, butyl hexanoate, diethyl sebacate, trans-2-hexen-1-ol, methyl nononoate, methyl 3-phenylpropionate, propyl heptanoate, propyl hexanoate, isopropyl phenylacetate, tributyl acetylcitrate, triethyl citrate, hexyl isobutyrate, cis-3-hexenyl butyrate, hexyl phenylacetate, methyl 3-hydroxyhexanoate, 3-methyl-1-pentanol, ethyl chrysanthemumate compounds.

The woody category of the fragrances can be formulated by incorporating allylα-ionone, d-camphor, 4-carvomethenol, β-caryophyllene, cuminaldehyde, 2',4'-dimethylacetopheone, furfural, 3-(2-fury)acrolein, guaiacol, heptanal, heptyl alcohol, hexyl alcohol, α-Ionone, β-Ionone, dl-menthol, dl-menthyl acetate, menthyl isovalerate, 4-methyl-1-phenyl-2-pentanone, nerolidol, 1-octanol, octyl isobutyrate, (1s)-(−)α-pinene, (1s)-(−)-β-penene, 3-propylidenephthalide, thymol, veratraldehyde, undecylenic acid, 2-sec-butylcyclohexanone, 2,5-dimethylpyrazine, 2-ethylpyrazine, 4-oxoisophorone, (1r)-(−)-myrtenol, m-cresol, isophorone, 2-methoxyphenyl acetate, cis-3-hexenyl benzoate, theaspirane, 4-isopropylphenol, 4-tert-butylcyclohexylacetate, 4-hydroxybenzaldehyde, 1-methylpyrrole, 3',4'-dimethoxyacetophenone compounds.

The container used to place the air fresheners can be of any size and shape such as circular, square, and rectangular. Preferably, the container may be placed inconspicuously into an automobile. The container may be prepared from plastic, ceramic, wood, paper board and metal. It is preferred that the container have air passageways to allow for the fragrance to escape into the surrounding environment.

The air freshener compositions contain 1 to 75 weight percent of the fiber pad and 25 to 99 weight percent of the fragrance. Preferably, the air freshener compositions contain 5 to 30 weight percent of the fiber pad and 70 to 95 weight percent of the fragrance.

The following examples are intended to illustrate, but not limit, the scope of this invention. All parts and percentages in the examples are on a weight basis unless otherwise stated.

EXAMPLE 1

This example illustrates the properties of a vanilla air freshener for ambient and elevated temperature applications. The ingredients and their amount used were as follows:

| Ingredients | Amount (g) | (%) |
| --- | --- | --- |
| Anisyl Alcohol | 6.0 | 30.0 |
| Anisyl Propionate | 6.0 | 30.0 |
| Ethyl Vanillin | 4.0 | 20.0 |
| Acetovanillin | 4.0 | 20.0 |

The ingredients were incorporated in a fiber pad as follows:

(I) A mixture of anisyl alcohol and anisyl propionate was prepared. A mixture of ethyl vanillin and acetovanillin was prepared. The mixtures were combined with stirring to prepare a fragrance mixture.

(II) The fragrance mixture was heated to 45°–60° C. to prepare a clear fragrance solution.

(III) The fragrance solution was incorporated into a needle-punched, non-woven, deep-grooved polyethylene terephthalate fiber pad having a capillary structure with a large surface area.

The fiber pad (0.35 g) was cut into a 1 inch×1 inch (2.54 cm) square. The clear fragrance mixture (3.0 g) was added to the fiber pad using a dropper. The liquid fragrances were absorbed into the pad. The pad appeared almost dry even after the addition of about ten times the amount of fragrance based on the weight of the fiber pad.

EXAMPLE 2

The fragrance pads prepared in Example 1 were examined for smell acceptance. The smell was rated by each member of a panel according to the following scale:

1. Poor: No smell detected.
2. Fair: Slight smell detected.
3. Good: Smell detected but too strong.
4. Excellent: Normal smell acceptance.

The panel members' rating was as follows:

| Panel Member (%) | Rating Scale |
| --- | --- |
| 90% | 4 |
| 5% | 3 |
| 5% | 2 |

These results indicate that 90% of the panel judged the smell originating from the air freshener to be at an acceptable level and neither too strong or mild.

EXAMPLE 3

Example 1 was repeated except that cherry fragrances were used instead of vanilla fragrances to formulate an air freshener. The ingredients and their amount used were as follows:

| Ingredients | Amount (g) | (%) |
|---|---|---|
| Piperonal | 6.0 | 30.0 |
| Butyrophenone | 6.0 | 30.0 |
| Amyl Butyrate | 8.0 | 40.0 |

The ingredients were loaded in a fiber pad by following procedure:

(I) Mixed butyrophenone and amyl butyrate fragrances.

(II) Added piperonal fragrance to the mixture.

(III) Mixed all fragrances at room temperature to form a clear fragrance solution.

A small amount (≈3.0 g) of clear fragrance solution was loaded into (≈0.36 g) of a needle-punched, non-woven, deep-grooved polyethylene terephthalate fiber pad, having a capillary structure with a large surface area, at room temperature. The fiber pad surface felt dry upon touching.

EXAMPLE 4

Example 2 was repeated except that air fresheners prepared in Example 3 were used instead of air fresheners prepared in Example 1 for evaluation of cherry fragrance by a panel. The panel members' rating of cherry fragrance was as follows:

| Panel Members | Rating Scale |
|---|---|
| 80% | 4 |
| 15% | 3 |
| 5% | 2 |

These results indicate that 80% of the panel judged the smell originating from the air freshener to be at an acceptable level and neither too strong or mild.

EXAMPLE 5

The vanilla fragrance prepared in Example 1 (2.92 g) was loaded into a needle-punched, non-woven, deep-grooved, hydrophilic polyethylene terephthalate fiber pad (0.38 g). The fiber pad was placed in a circular container having several holes to allow for the fragrance to escape. The container was kept at ambient temperature (22.5° C.).

The fiber pad was weighed once a week. No significant weight change was observed after eight weeks. The vanilla smell rating was determined to be 4, according to the test method set forth in Example 2, by 90% of the panel members after the eight week period. Thus, this data shows an excellent stability of the air freshener at room temperature.

EXAMPLE 6

Example 5 was repeated except that fragrance loss was measured at 50° C. in an oven with air flow instead of room temperature. The vanilla fragrance (2.88 g) was loaded in a polyethylene terephthalate fiber pad (0.42 g). The fiber pad was placed in a circular container which had several holes to allow the fragrance to escape. The container was placed in an oven with air flow at 50° C. The container was removed from the oven and weighed once a week to determine weight loss of the fragrance. The following data was recorded:

| Time (Week) | Fragrance Weight (g) | Weight Loss (%) |
|---|---|---|
| 0 | 2.88 | 0 |
| 1 | 2.81 | 2.4 |
| 3 | 2.48 | 13.9 |
| 4 | 2.29 | 20.5 |

The data indicates that after four weeks at 50° C., 20.5 wt. % of the fragrance escaped. In addition, the vanilla smell rating was determined to be 4, according to the test method set forth in Example 2, by 90% of the panel members after the four week period. Thus, this data shows an excellent stability of the air freshener at high temperatures.

EXAMPLE 7

Example 6 was repeated except that fragrance loss was measured at 50° C. in an oven without air flow instead of in an oven with air flow. This example illustrates the effect of air flow on the release of the fragrances.

The vanilla fragrance (2.60 g) was loaded in a polyethylene terephthalate fiber pad (0.35 g). The fiber pad was placed in a circular container which had several holes to allow for the fragrance to escape. The container was placed in an oven without air flow at 50° C. The container was removed from the oven and weighed once a week to determine weight loss of the fragrance.

Results indicated that only about 4 wt % of the fragrance was lost after four weeks. In comparison, the data from Example 6 indicated that after four weeks at 50° C. in an oven with air flow, 20.5 wt. % of the fragrance escaped. Thus, the release of the fragrances was activated to a greater degree by air flow. Even without air flow, the vanilla smell rating was determined to be 4, according to the test method set forth in Example 2, by 90% of the panel members after a four week period.

EXAMPLE 8

This example illustrates the importance of a needle-punched, non-woven, deep-grooved polyethylene terephthalate fiber pad having a capillary structure with a large surface area in air freshener compositions which are subjected to high temperature applications. The fragrances and their amount used were as follows:

| Ingredients | Amount (g) | (%) |
|---|---|---|
| Anisyl Alcohol | 6.0 | 30.0 |
| Anisyl Propionate | 6.0 | 30.0 |
| Ethyl Vanillin | 4.0 | 20.0 |
| Acetovanillin | 4.0 | 20.0 |

A fragrance solution was prepared as follows:

(I) A mixture of anisyl alcohol and anisyl propionate was prepared. A mixture of ethyl vanillin and acetovanillin was prepared. The mixtures were combined with stirring to prepare a fragrance mixture.

(II) The fragrance mixture was heated to 45°–60° C. to prepare a clear fragrance solution.

The clear fragrance solution (2.60 g) was placed in an aluminum container. The container was covered with metal foil which had several passageways to allow for escape of the fragrance. The container was placed in an oven with air flow at 50° C. The container was removed from the oven and weighed once a week to determine weight loss of the fragrance. The following data was recorded:

| Time (Week) | Fragrance Weight (g) | Weight Loss (wt. %) |
| --- | --- | --- |
| 0 | 2.60 | 0 |
| 1 | 1.04 | 60.0 |
| 3 | 0.23 | 91.15 |
| 4 | 0.16 | 93.85 |
| 5 | 0.14 | 94.62 |

The data indicates that after four weeks at 50° C., 93.85 weight percent of the fragrance escaped. Comparing the data in Example 8 with the data in Example 6 wherein the fragrance solution was incorporated into a fiber pad indicates that fragrance loss is about 73.35 wt. % greater without a fiber pad over a period of four weeks at 50° C. Thus, the large surface area provided by capillary structure of the fiber pad retains the fragrances for a longer period of time as compared to fragrances not incorporated into a fiber pad.

EXAMPLE 9

Example 5 was repeated except that fragrance loss was measured at 125° C. in an oven with air flow instead of room temperature. The vanilla fragrance (2.60 g) was loaded in a polyethylene terephthalate fiber pad (0.35 g). The fiber pad was placed in a circular container having holes to allow for the fragrance to escape. The container was placed in an oven at 125° C. The weight of the fragrance reduced from 2.60 g to 0.76 g in one-week.

About 70.0 wt % of the vanilla fragrance was lost after one week at 125° C in an oven with air flow. The vanilla smell rating was determined to be 4, according to the test method set forth in Example 2, by 90% of the panel members after a one week period.

EXAMPLE 10

Example 9 was repeated except that the clear fragrance solution was loaded in a cotton ball instead of fiber pad. The vanilla fragrance (2.60 g) was loaded in the cotton ball (0.36 g). The cotton ball was placed in a circular container having holes to allow for the fragrance to escape. The container was placed in an oven at 125° C.

The weight of the vanilla fragrance was decreased by 98 wt. % after one week in the oven with air flow at 125° C. In comparision, 70 wt % of the vanilla fragrance was lossed after one week at 125° C. in an oven with air flow in Example 9 wherein the fragrance was incorporated into a fiber pad. Thus, the data indicates that the fiber pad retains fragrances longer than other substrates such as cotton.

Many variations will suggest themselves to those skilled in this art in light of the above detailed description. All such obvious modifications are within the full intended scope of the appended claims.

What is claimed is:

1. An air freshener composition comprising:

(A) 1 to 75 weight percent of a fiber pad comprising at least one needle-punched, nonwoven, hydrophilic fiber wherein the fiber has a capillary structure and at least one deep groove along the longitudinal axis of the fiber; and (B) 25 to 99 weight percent of at least one fragrance incorporated into said fiber pad.

2. The air freshener composition according to claim 1, for ambient and high temperature applications comprising:

(A) 1 to 75 weight percent of a fiber pad comprising at least one needle-punched, nonwoven, hydrophilic fiber wherein the fiber has a capillary structure and at least one deep groove along the longitudinal axis of the fiber; and (B) 25 to 99 weight percent of at least one fragrance incorporated into said fiber pad, wherein the fiber pad is enclosed by a containner having air passageways to allow for the fragrance to escape into the surrounding environment.

3. The air freshener composition according to claim 2, comprising:

(A) 5 to 30 weight percent of a fiber pad comprising at least one needle-punched, nonwoven, hydrophilic fiber wherein the fiber has a capillary structure and at least one deep groove along the longitudinal axis of the fiber; and (B) 70 to 95 weight percent of at least one fragrance incorporated into said fiber pad.

4. The air freshener composition according to claim 1 wherein the fiber is selected from the group consisting of polyesters, copolyesters, cellulose acetate, olefins, nylon, modacrylate, polyphenylene sulfide, viscose rayon, fibers made from biodegradable materials, and combinations thereof.

5. The air freshener composition according to claim 1 wherein the fiber is prepared from filaments which have a denier per filament of 3 to 1,000.

6. The air freshener composition according to claim 5 wherein the filaments have a denier per filament of 5 to 30.

7. The air freshener composition according to claim 5 wherein the polymer is selected from the group consisting of relatively unoriented and relatively oriented polyethylene terephthalate, copolyesters based on polyethylene terephthalate, polyethylene terephthalate containing cellulosic additives and/or modified starch, and cellulose acetate.

8. The air freshener composition according to claim 6 wherein the fiber is polyethylene terephthalate.

9. The air freshener composition according to claim 1 wherein the fragrance is selected from the group consisting of alliaceous, animal, balsanic, camphoraceous, chemical, cherry, citrus, coffee, earthy, ethereal, fatty, floral, fruity, green, herbaceous, lemon, meaty, medicinal, minty, mossy, musty, new car scent, nutty, pepper, pine, pineapple, potpourri, smoky, soapy, spicy, sulfurous, vegetable, vanilla, waxy, wine-like, woody, and combinations thereof.

10. The air freshener composition according to claim 1 wherein the fragrance is selected from the group consisting of cherry, lemon, vanilla, pine, pineapple, potpourri, floral, and new car scent.

11. The air freshener composition according to claim 2 wherein the container is prepared from a material selected from the group consisting of plastic, ceramic, wood, paper board, metal, and combinations thereof.

12. An air freshener comprising:

1 to 75 weight percent of a fiber pad comprising at least one needle-punched, nonwoven, hydrophilic fiber wherein the fiber is prepared from filaments that are capable of spontaneously transporting fluids, said filaments described by the equation:

$$(1-X \cos \Theta_a) < 0$$

wherein: $\Theta_a$ is the advancing contact angle of water measured on a flat film made from the same material as the filament and having the same surface treatment, if any, and X is a shape factor of the filament cross-section that satisfies the following equation:

$$X = P_w/(4r+(\pi-2)D)$$

wherein $P_w$ is the wetted perimeter of the filament, r is the radius of the circumscribed circle circumscribing the filament cross-section, and D is the minor axis demension across the filament cross-section, said fiber further characterized by having at least one groove along the longitudinal axis of the fiber; and 25 to 99 weight percent of at least one fragrance incorporated into said fiber pad.

13. The air freshener according to claim 12, wherein the fiber pad is enclosed by a container having air passageways to allow for the fragrance to escape into the surrounding environment.

14. The air freshener according to claim 13, wherein the surface of said fiber has a hydrophilic lubricant coated thereon.

15. The air freshener according to claim 12, wherein said fiber pad comprises fiber selected from the group consisting of polyesters, cellulose acetate, and mixtures thereof.

16. The air fresheners according to claim 12, wherein said fiber pad comprises a polyester or copolyester containing polyethylene terephthalate.

* * * * *